(12) United States Patent
Krebs et al.

(10) Patent No.: US 9,707,008 B2
(45) Date of Patent: Jul. 18, 2017

(54) SYSTEMS AND METHODS FOR TREATING POST-OPERATIVE INFECTIONS

(71) Applicant: THE CLEVELAND CLINIC FOUNDATION, Cleveland, OH (US)

(72) Inventors: Viktor E. Krebs, Rocky River, OH (US); Wael K. Barsoum, Bay Village, OH (US); Bret E. Hartzell, Massillon, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 744 days.

(21) Appl. No.: 14/151,878

(22) Filed: Jan. 10, 2014

(65) Prior Publication Data

US 2014/0194811 A1 Jul. 10, 2014

Related U.S. Application Data

(60) Provisional application No. 61/750,946, filed on Jan. 10, 2013.

(51) Int. Cl.
*A61B 17/34* (2006.01)
*A61B 17/72* (2006.01)
(Continued)

(52) U.S. Cl.
CPC .......... *A61B 17/3421* (2013.01); *A61B 17/72* (2013.01); *A61F 2/38* (2013.01);
(Continued)

(58) Field of Classification Search
CPC ....... A61B 17/3421; A61B 17/72; A61F 2/38; A61F 2002/30616; A61F 2002/30672;
(Continued)

(56) References Cited

U.S. PATENT DOCUMENTS

| 5,433,718 A | 7/1995 | Brinker | |
|---|---|---|---|
| 2010/0217401 A1* | 8/2010 | de Beaubien | A61F 2/36 623/20.34 |
| 2014/0277532 A1* | 9/2014 | Teeny | A61F 2/38 623/20.24 |

OTHER PUBLICATIONS

Duncan et al., "The Role of Antibiotic-Loaded Cement in the Treatment of an Infection After a Hip Replacement", The Journal of Bone and Joint Surgery, 76A, Nov., No. 11, pp. 1742-1751.
(Continued)

*Primary Examiner* — Laura Bouchelle
*Assistant Examiner* — Justin L Zamory
(74) *Attorney, Agent, or Firm* — Tarolli, Sundheim, Covell & Tummino LLP

(57) ABSTRACT

An infection treatment system includes a first intramedullary rod for placement within an intramedullary canal and including a superior portion having a superior end, an inferior portion having an inferior end, and a shaft extending longitudinally between the superior and inferior portions. The shaft includes longitudinally extending channels. A second intramedullary rod for placement within an intramedullary canal includes a superior portion having a superior end, an inferior portion having an inferior end, and a shaft extending longitudinally between the superior and inferior portions. The shaft includes longitudinally extending channels. A coupler is operatively attached to the rods. The coupler has a superior face, an inferior face, an anterior face, a posterior face, a first lateral face and a second lateral face. At least one of the faces includes at least one opening in fluid communication with at least a portion of the channels of the first and second rods.

21 Claims, 13 Drawing Sheets

(51) Int. Cl.
*A61M 1/00* (2006.01)
*A61M 5/142* (2006.01)
*A61M 5/168* (2006.01)
*A61F 2/38* (2006.01)
A61F 2/30 (2006.01)
A61F 2/36 (2006.01)
A61F 2/46 (2006.01)

(52) U.S. Cl.
CPC .......... *A61M 1/0023* (2013.01); *A61M 5/142* (2013.01); *A61M 5/16881* (2013.01); *A61F 2002/30616* (2013.01); *A61F 2002/30672* (2013.01); *A61F 2002/30677* (2013.01); *A61F 2002/3694* (2013.01); *A61F 2002/4685* (2013.01)

(58) Field of Classification Search
CPC .... A61F 2002/30677; A61F 2002/3694; A61F 2002/4685; A61F 2002/3068; A61F 2002/3621; A61F 2002/368
See application file for complete search history.

(56) References Cited

OTHER PUBLICATIONS

PCT International Search Report and Written Opinion for PCT/US2014/010961, mailed Jun. 10, 2014, pp. 1-16.

\* cited by examiner

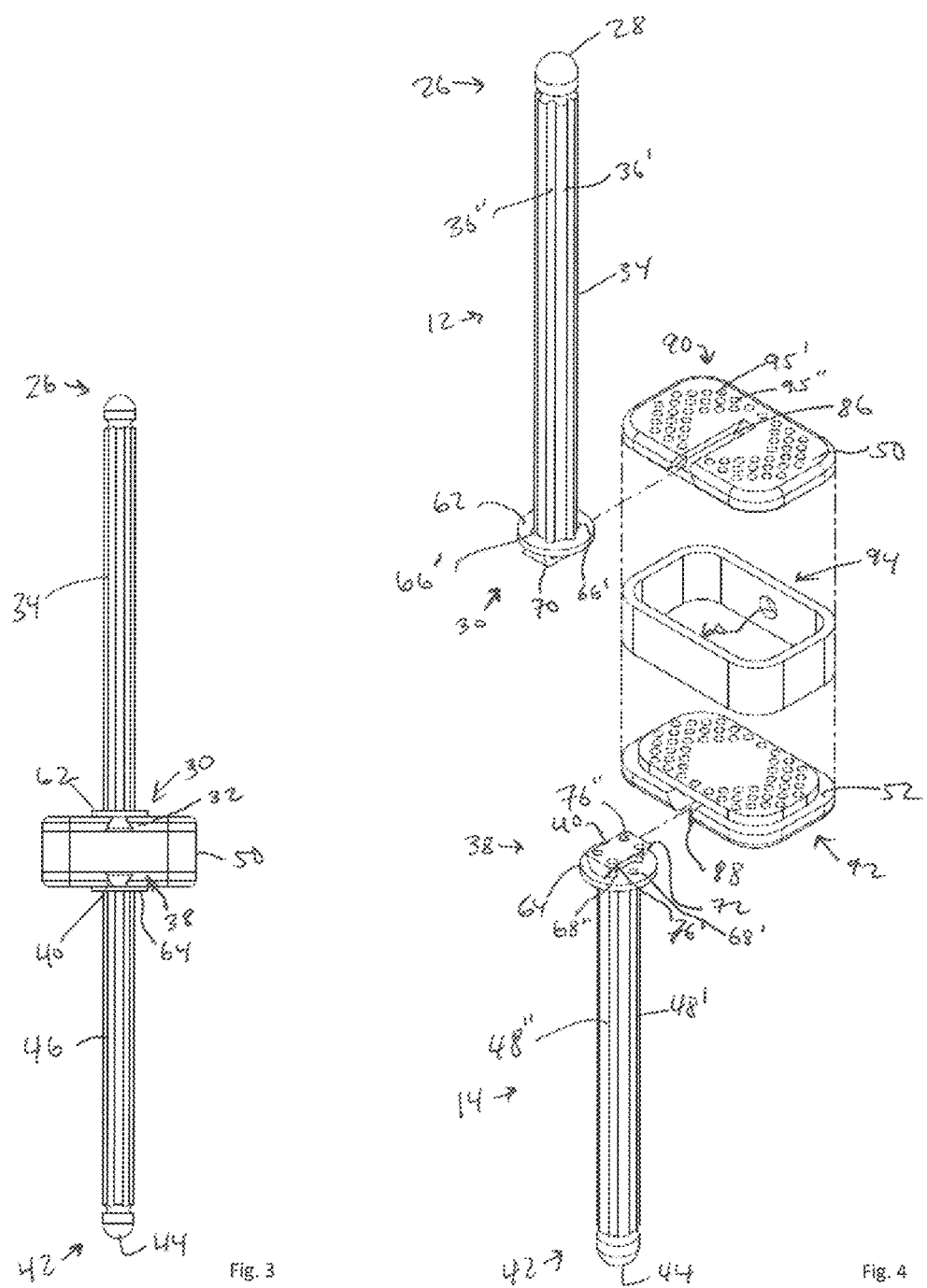

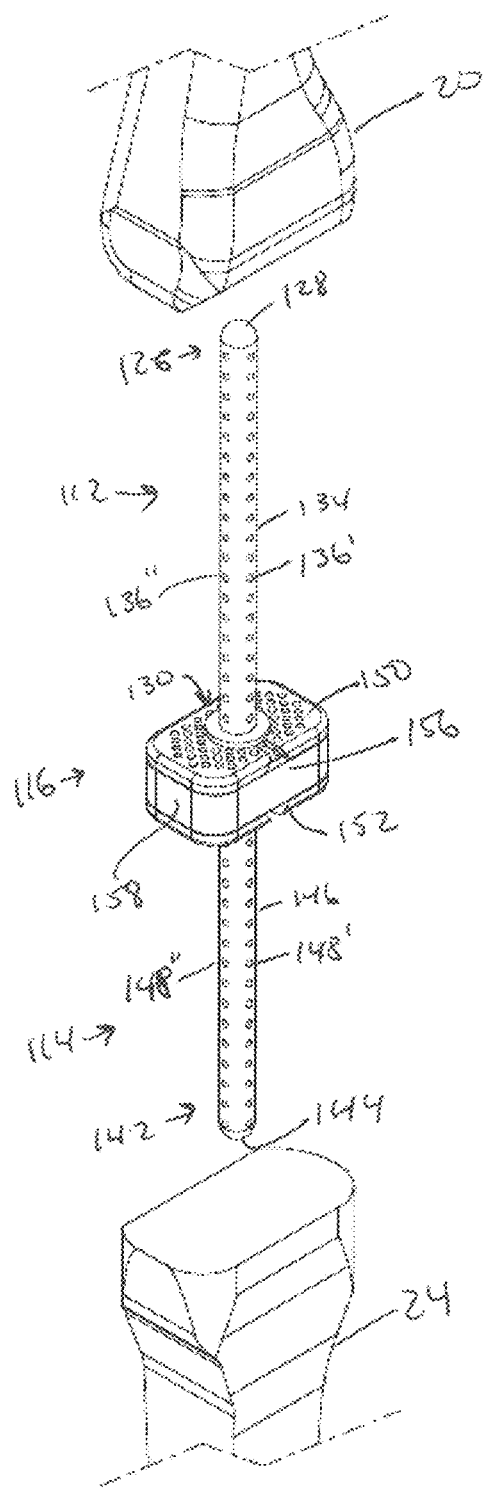
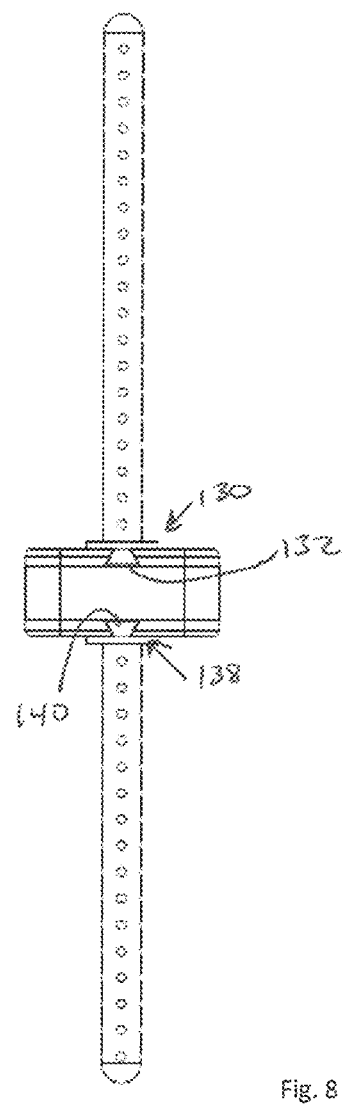
Fig. 7
Fig. 8

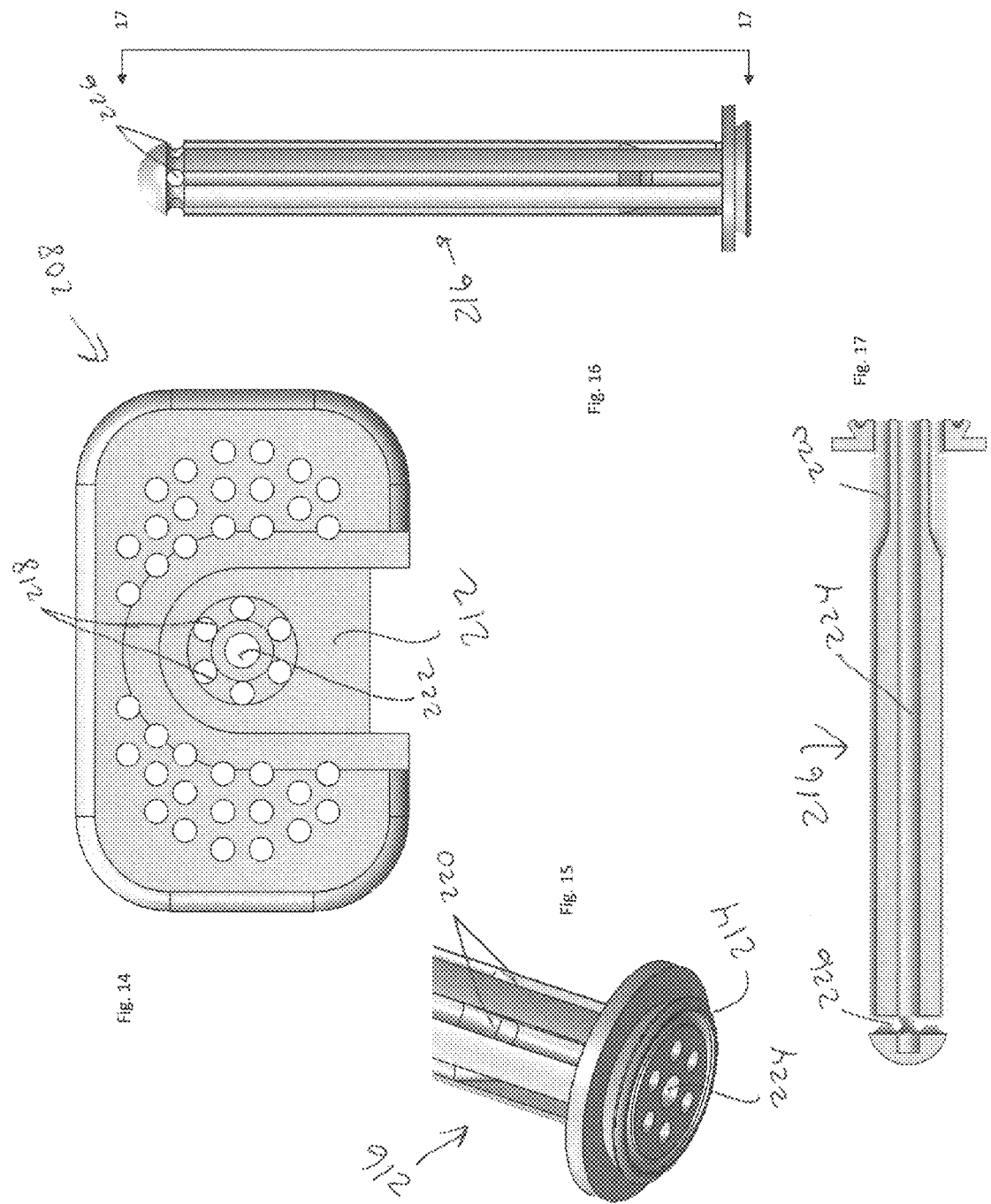

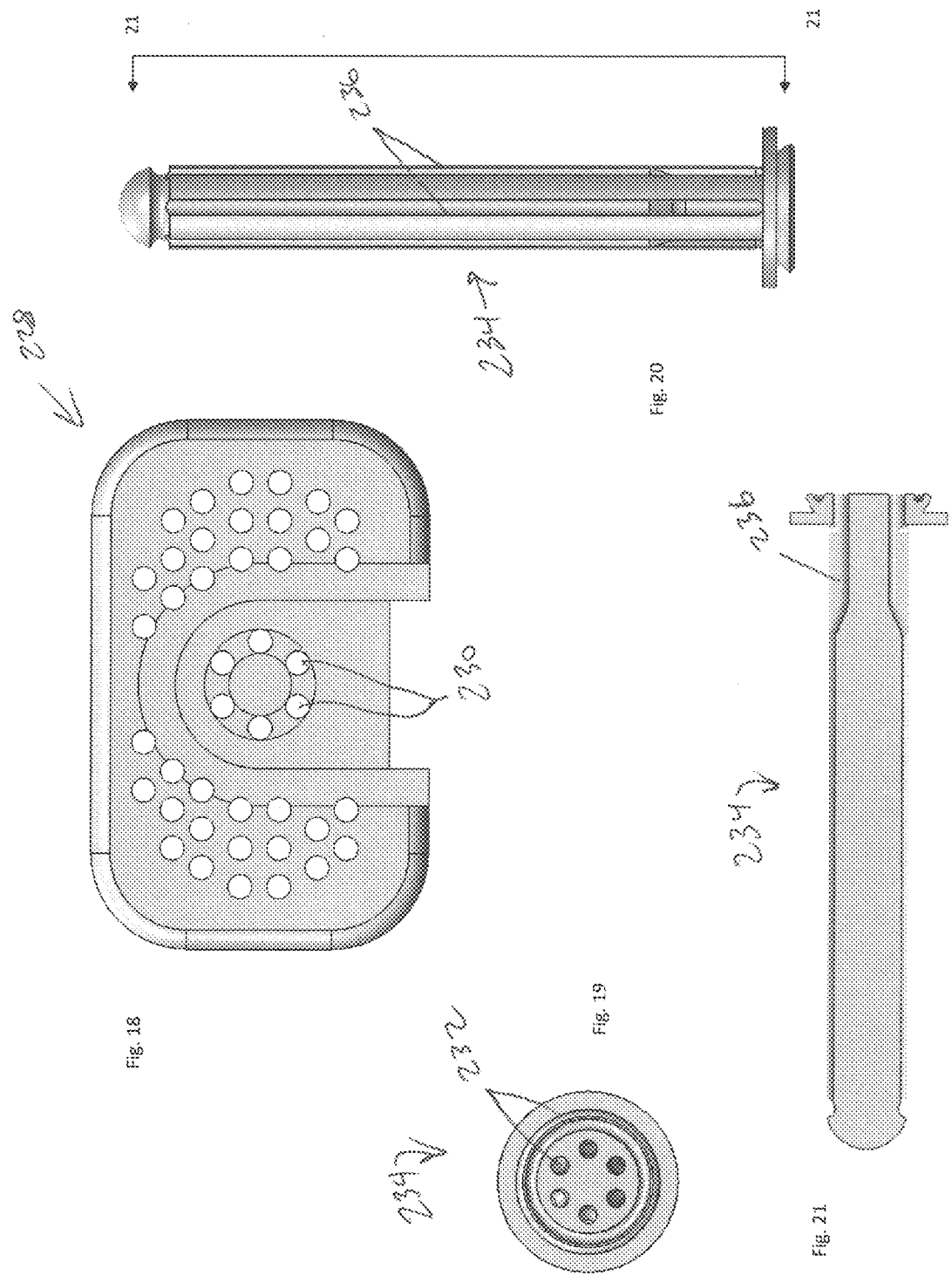

SYSTEMS AND METHODS FOR TREATING POST-OPERATIVE INFECTIONS

RELATED APPLICATION

This application claims priority from U.S. Provisional Application No. 61/750,946, filed 10 Jan. 2013, the subject matter of which is incorporated herein by reference in its entirety.

TECHNICAL FIELD

The present invention is directed to systems and methods of treating infections that occur after implantation of a medical device in a joint space.

BACKGROUND

Total knee arthroplasty ("TKA") carries certain risks, including the risk of implantation degradation and failure, loosening of aseptic hardware, deep vein thrombosis, and infection. Infection is frequently the cause of implantation failure. TKA is becoming more common as the population continues to age. The increasing number of these procedures means that the number of infected arthroplasties will increase as well (See Kotelnicki, J. "Surgical treatment for patients with an infected total knee arthroplasty," *Journal of the American Academy of Physician Assistants*, (Nov. 23, 2009).

A current treatment for TKA is an antibody impregnated device that is placed within the joint space of the infection site. Such devices, however, do not treat both the joint space and the intramedullary canal. Further, such devices do not remove infectious material from the infection site.

SUMMARY

In an embodiment of the present invention, an infection treatment system is provided. A first intramedullary rod is configured for placement within an intramedullary canal. The first rod comprises a superior portion having a superior end, an inferior portion having an inferior end, and a shaft having a longitudinal axis therethrough and extending between the superior and inferior portions. The shaft comprises a plurality of elongate angularly spaced channels extending substantially parallel to the longitudinal axis of the shaft. A second intramedullary rod is configured for placement within an intramedullary canal. The second rod comprises a superior portion having a superior end, an inferior portion having an inferior end, and a shaft having a longitudinal axis therethrough extending between the superior and inferior portions. The shaft comprises a plurality of elongate angularly spaced channels extending substantially parallel to the longitudinal axis of the shaft. A fenestrated coupler is attached to the first and second rods in an operative configuration. The fenestrated coupler has a superior face, an inferior face, an anterior face, a posterior face, a first lateral face and a second lateral face. At least one of the faces comprises at least one opening in fluid communication with at least a portion of the plurality of channels of the first and second rods.

In an embodiment of the present invention, an infection treatment system is provided. A first intramedullary rod is configured for placement within an intramedullary canal. The first rod comprises a superior portion having a superior end, an inferior portion having an inferior end, and a shaft having a longitudinal axis therethrough and extending between the superior and inferior portions. The shaft comprises a plurality of elongate angularly spaced channels extending substantially parallel to the longitudinal axis of the shaft. The inferior portion comprises a base plate defining an array of apertures in fluid communication with the plurality of channels and comprises a fastener depending from the base plate. The fastener comprises at least one opening in fluid communication with the array of apertures. The superior portion comprises a circumferential groove and a stopper superior to the groove. The stopper has an outer diameter equal to or greater than the outer diameter of the shaft. A second intramedullary rod is configured for placement within an intramedullary canal. The second rod comprises a superior portion having a superior end, an inferior portion having an inferior end, and a shaft having a longitudinal axis therethrough and extending between the superior and inferior portions. The shaft comprises a plurality of elongate angularly spaced channels along the longitudinal axis of the shaft. The superior portion comprises a base plate defining an array of apertures in fluid communication with the plurality of channels and comprising a fastener extending from the base plate. The fastener comprises at least one opening in fluid communication with the array of apertures. The inferior portion comprises a circumferential groove and a stopper inferior to the groove. The stopper has an outer diameter equal to or greater than the outer diameter of the shaft. A fenestrated coupler has a superior face, an inferior face, an anterior face, a posterior face, a first lateral face and a second lateral face. A first one of the faces comprises an opening in fluid communication with at least one of the arrays of apertures of the first and second rods. A second one of the faces comprises a fastener complementary to the fastener of the first rod and an opposing third one of the faces comprises a fastener complementary to the fastener of the second rod.

In an embodiment of the present invention, an infection treatment system is provided. A cannulated first intramedullary rod is configured for placement within an intramedullary canal. The first rod comprises a superior portion having a superior end, an inferior portion having an inferior end, and a shaft having a lumen and longitudinal axis therethrough and extending between the superior and inferior portions. The shaft comprises a plurality of angularly spaced openings extending along the longitudinal axis. A cannulated second intramedullary rod is configured for placement within an intramedullary canal. The second rod comprises a superior portion having a superior end, an inferior portion having an inferior end, and a shaft having a lumen and a longitudinal axis therethrough and extending between the superior and inferior portions. The shaft comprises a plurality of angularly spaced openings extending along the longitudinal axis. A fenestrated coupler is attached to the first and second rod in an operative configuration. The fenestrated coupler has a superior face, an inferior face, an anterior face, a posterior face, a first lateral face and a second lateral face. At least one of the faces comprises at least one opening in fluid communication with the plurality of openings of the first and second rods and at least one of the faces comprises at least one opening in fluid communication with the lumen of a corresponding one of the first and second rods.

In an embodiment of the present invention, an infection treatment system is provided. A cannulated first intramedullary rod is configured for placement within an intramedullary canal. The first rod comprises a superior portion having a superior end, an inferior portion having an inferior end, and a shaft having a lumen and a longitudinal axis therethrough and extending between the superior and inferior portions. The shaft comprises a plurality of angularly spaced openings extending along the longitudinal axis. The inferior portion comprises a fastener comprising an opening in fluid communication with the lumen. A cannulated second intramedullary rod is configured for placement within an intramedullary canal. The second rod comprises a superior portion having a superior end, an inferior portion having an inferior end, and a shaft having a lumen and a longitudinal axis therethrough and extending between the superior and inferior portions. The shaft comprises a plurality of angularly spaced openings extending along the longitudinal axis. The superior portion comprises a fastener comprising an opening in fluid communication with the lumen. A fenestrated coupler has a superior face, an inferior face, an anterior face, a posterior face, a first lateral face and a second lateral face. A first one of the faces comprises an opening in fluid communication with the openings of the first and second fasteners of the first and second rods, a second one of the faces comprises a fastener complementary to the fastener of the first rod, and an opposing third one of the faces comprises a fastener complementary to the fastener of the second rod.

BRIEF DESCRIPTION OF THE DRAWINGS

For a better understanding of the invention, reference may be made to the accompanying drawings, in which:

FIG. 3 is a posterior view of the embodiment of FIG. 1;

FIG. 4 is an exploded view of the embodiment of FIG. 1;

FIG. 7 is a perspective view of an embodiment of the present invention in an example use environment;

FIG. 8 is a posterior view of the embodiment of FIG. 7;

FIG. 14 is a plan view of the component of FIG. 12;

FIG. 15 is a partial perspective view of another component for use with the component of FIG. 12;

FIG. 16 is a side view of the component of FIG. 15;

FIG. 17 is a cross-sectional view taken along line 17-17 of FIG. 15;

FIG. 18 is a plan view of a component for use with any embodiment of the present invention;

FIG. 19 is a partial perspective view of another component for use with the component of FIG. 18;

FIG. 20 is a side view of the component of FIG. 19;

FIG. 21 is a cross-sectional view taken along line 21-21 of FIG. 20;

DETAILED DESCRIPTION

The present invention provides systems and methods which may be used for post-operatively treating patients with infections within a joint space and/or intramedullary canal(s) after implantation of a medical device, such as a prosthesis, in a joint space. In particular, the present invention provides systems that may be employed as part of a revision surgery to treat the infection site after removal of an existing medical device and prior to implantation of a new medical device in the joint space. Embodiments of the present invention may facilitate the introduction and extraction of a therapeutic fluid into and out of the joint space and intramedullary canals. Additionally or alternatively, the present invention could be used in a non-joint space and/or for fluid communication for any reason (i.e., not necessarily infection treatment) in any patient tissue. Although the present invention will be described with respect to a post-operative TKA infection, it is understood that the present invention can also be employed to treat other types of joint infections following implantation of a medical device (such as, for example, hip, shoulder, and elbow infections) or either joint or non-joint infections in any suitable patient tissue.

Figures 1, 2:
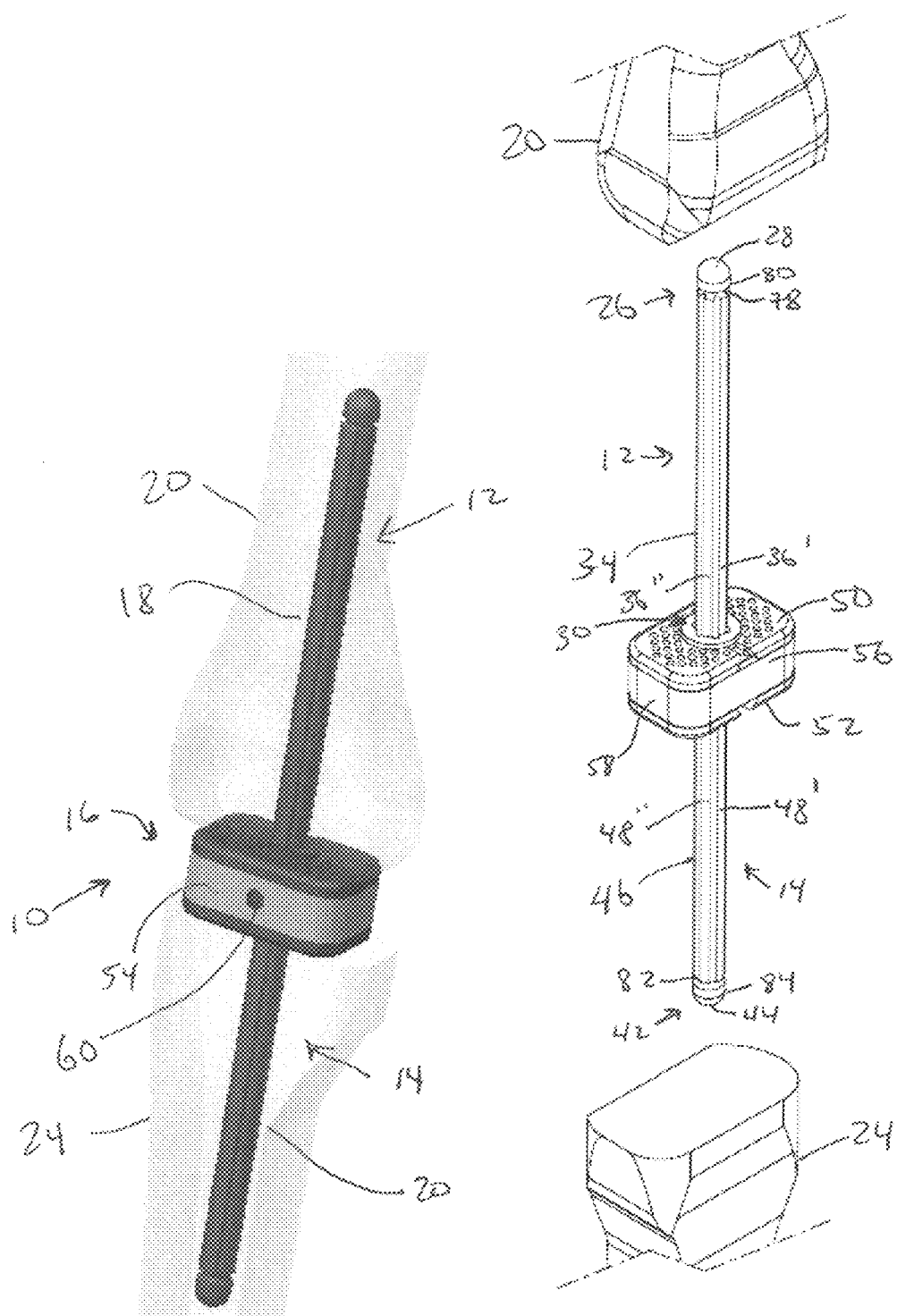
FIG. 1 is a perspective view of an embodiment of the present invention in an example use environment.
FIG. 2 is a perspective view of the embodiment of FIG. 1.

In accordance with the present invention, FIG. 1 depicts an infection treatment system 10 comprising a first intramedullary rod 12, a second intramedullary rod 14, and a fenestrated coupler 16. First intramedullary rod 12 is configured for placement in an intramedullary canal. FIG. 1 illustrates first rod 12 positioned in the femoral intramedullary canal 18 of the patient's femur 20 and second rod 14 positioned in the tibial intramedullary canal 22 of the patient's tibia 24. Referring to FIGS. 2 and 3, first rod 12 comprises a superior portion 26 having a superior end 28, an inferior portion 30 having an inferior end 32, and a shaft 34 having a longitudinal axis therethrough and extending between the superior and inferior portions 26 and 30. Shaft 34 comprises a plurality of elongate angularly spaced channels 36 which extend substantially parallel to a longitudinal axis of the shaft 34.

Second rod 14 comprises a superior portion 38 having a superior end 40, an inferior portion 42 having an inferior end 44, and shaft 46 having a longitudinal axis therethrough and extending between superior and inferior portions 38 and 42. As with first rod 12, shaft 46 of second rod 14 comprises a plurality of elongate angularly spaced channels 48 extending substantially parallel to the longitudinal axis of shaft 46.

Fenestrated coupler 16 is attached to first and second rods 12 and 14 in an operative configuration of the system. Coupler 16 may be removably attached to first and second rods 12 and 14 as generally illustrated in FIG. 3 and as explained in more detail below. Fenestrated coupler 16 has a superior face 50, an inferior face 52, an anterior face 54, a posterior face 56, a first lateral face 58 and a second lateral face (not shown). One of the faces of coupler 16 comprises at least one opening 60 in fluid communication with the plurality of channels 36 and 48 of first and second rods 12 and 14. In FIG. 1, opening 60 is defined by the anterior face 54 of coupler 16 but could be defined by another face of the coupler.

In an example embodiment, inferior portion 30 of first rod 12 and superior portion 38 of second rod 14 comprise a base plate 62 and 64 respectively as seen in FIG. 4. The base plates 62 and 64 comprise at least one array of apertures 66 and 68 in fluid communication with the plurality of channels 36 and 48 respectively. The array of apertures are also in fluid communication with at least one opening 60 of coupler 16 to provide a passageway for fluid to flow into channels 36 and 48 when the system is in an operative configuration. The array of apertures of the first rod's base plate and the array of apertures of the second rod's base plate can be in registration with the respective shaft's plurality of channels to provide smooth fluid flow between the apertures and channels.

Figure 5:
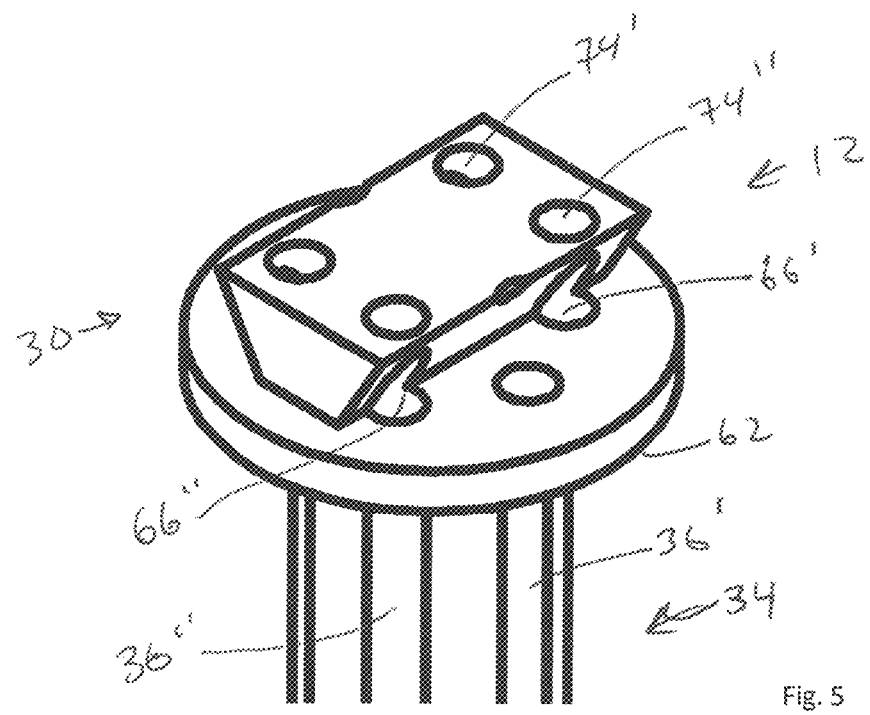
FIG. 5 is a partial view of a component of the embodiment of FIG. 1.

Inferior portion 30 of first rod 12 may comprise fastener 70 depending from base plate 62 and superior portion 38 of second rod 12 also comprises a fastener 72 extending from base plate 64. Fasteners 70 and 72 may comprise at least one opening 74 and 76 in fluid communication with the array of apertures of base plate 62 and 64 respectively as seen in FIG. 4 and FIG. 5. Optionally, each of the fasteners may comprise a plurality of openings. Openings 74 and 76 are also in fluid communication with at least one opening 60 of coupler 16 to provide a passageway for fluid to flow into channels 36 and 48 when the system is in an operative configuration.

Figure 6:
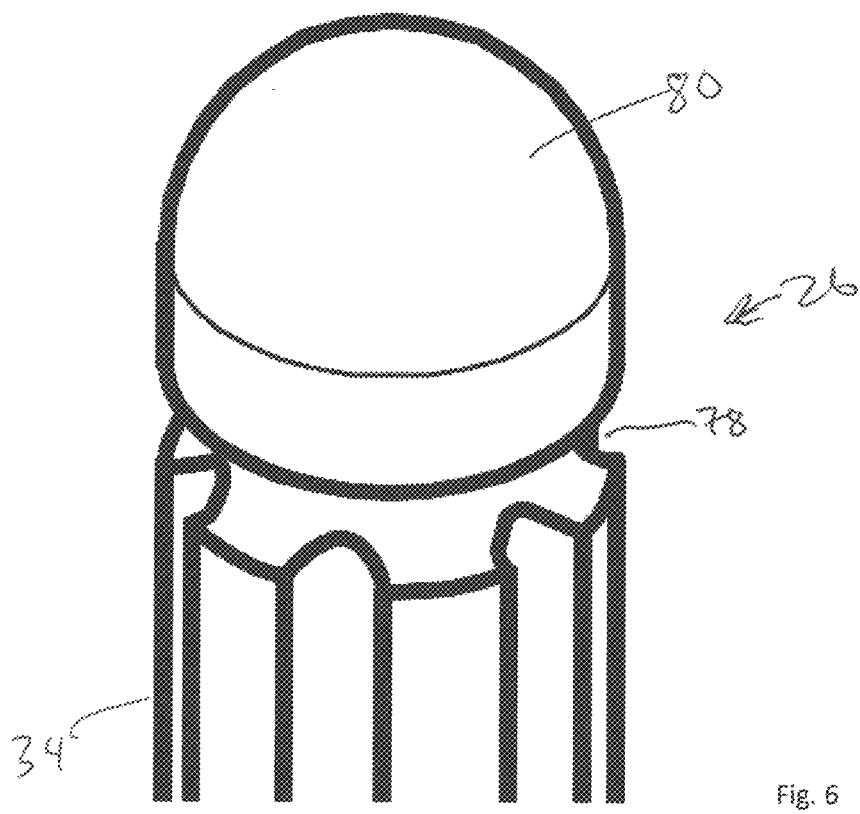
FIG. 6 is a partial view of another feature of the component of FIG. 5

Referring to FIG. 1 and FIG. 6, superior portion 26 of first rod 12 may comprise a circumferential groove 78 and a stopper 80 superior to groove 78. Stopper 80 is essentially at the superior end 28 of superior portion 26 of first rod 12. Similarly, inferior portion 42 of second rod 14 comprises a circumferential groove 82 and a stopper 84 inferior to groove 82. Stopper 84 is essentially at the inferior end 44 of inferior portion 42 of second rod 14. Stoppers 80 and 84 may have an outer diameter that is equal to or greater than the outer diameter of shaft 34 and 46, respectively.

At least one opening 60 of coupler 16 may be in fluid communication with a respective array of apertures 66 and 68 of base plates 62 and 64. In embodiments where fasteners 70 and 72 comprise one or more openings, at least one opening 60 is in fluid communication with such openings to provide a passageway for fluid to flow into channels 36 and 48 via the openings 74 and 76 of respective fasteners 70 and 72. As depicted in FIG. 4, one face of coupler 16 comprises a fastener 86 that is complementary to fastener 70 of first rod 12 and an opposing face of coupler 16 comprises a fastener 88 that is complementary to fastener 72 of second rod 14. As such, the fasteners of the coupler mate with the fasteners of the first and second rod. The fastening mechanism between the coupler and the first and second rods may be configured such that the coupler is removably coupled to the rods.

The fastening connection between the coupler and the rods can be any type of fastening connection that allows the rods to be securably coupled to the rod in an operative configuration of the system. The fastening connection may be a male/female connection. For example, as depicted in FIG. 4, fastener 70 and fastener 72 comprise male fasteners and fasteners 86 and 88 of coupler 16 comprise female fasteners. As depicted in FIG. 4, fastener 70 and fastener 72 may comprise a male dovetail fastener and fastener 86 and fastener 88 may comprise a female dovetail fastener. Although FIG. 4 depicts superior face 50 and inferior face 52 of coupler 16 comprising fasteners 86 and 88 respectively, any opposing faces of the coupler can comprise the fasteners that mate with the fasteners of the first and second rods, so long as fluid flow to the plurality of the rods' channels is not blocked.

In another embodiment, the present invention provides an infection treatment system that comprises cannulated intramedullary rods having shafts comprising a plurality of angularly spaced openings extending substantially parallel to the longitudinal axis of the shafts instead of or in addition to a plurality of elongate angularly spaced channels. In particular, referring to FIG. 7, this embodiment provides an infection treatment system 100 comprising a cannulated first intramedullary rod 112, a cannulated second intramedullary rod 114, and a fenestrated coupler 116. First and second intramedullary rods 112 and 114 are configured for placement in intramedullary canals.

First rod 112 comprises a superior portion 126 having a superior end 128, an inferior portion 130 having an inferior end 132, and a shaft 134 having a lumen and a longitudinal axis therethrough and extending between the superior and inferior portions 126 and 130. Shaft 134 comprises a plurality of elongate angularly spaced openings 136 extending substantially parallel to the longitudinal axis of shaft 134.

Second rod 114 comprises a superior portion 138 having a superior end 140, an inferior portion 142 having an inferior end 144, and shaft 146 having a lumen and a longitudinal axis therethrough and extending between superior and inferior portions 138 and 142. As with first rod 112, shaft 146 of second rod 114 comprises a plurality of elongate angularly spaced openings 148 extending substantially parallel to the longitudinal axis of shaft 146.

Fenestrated coupler 116 is attached to first and second rods 112 and 114 in an operative configuration of the system. Coupler 116 may be removably attached to first and second rods 112 and 114 as described above and as illustrated in FIG. 8. Fenestrated coupler 116 has a superior face 150, an inferior face 152, an anterior face (not shown), a posterior face 156, a first lateral face 158 and a second lateral face (not shown). One of the faces of coupler 116 comprises at least one opening (similar to opening 60 in FIG. 1) in fluid communication with the plurality of openings 136 and 148 of first and second rods 112 and 114. The coupler's opening(s) may be defined by the anterior face of coupler 116 but could be defined by another face of the coupler.

In certain embodiments employing cannulated intramedullary rods, inferior portion 130 of the first rod 112 comprises a fastener 170 and superior portion 138 of second rod 114 comprises a fastener 172. Each fastener 170 and 172 comprises at least one opening (shown in FIG. 9 as 176) in fluid communication with the lumen of the respective shafts 134 and 146. In certain embodiments, fastener 170 depends from a base plate 162 and fastener 172 extends from a base plate 164.

Figure 9:
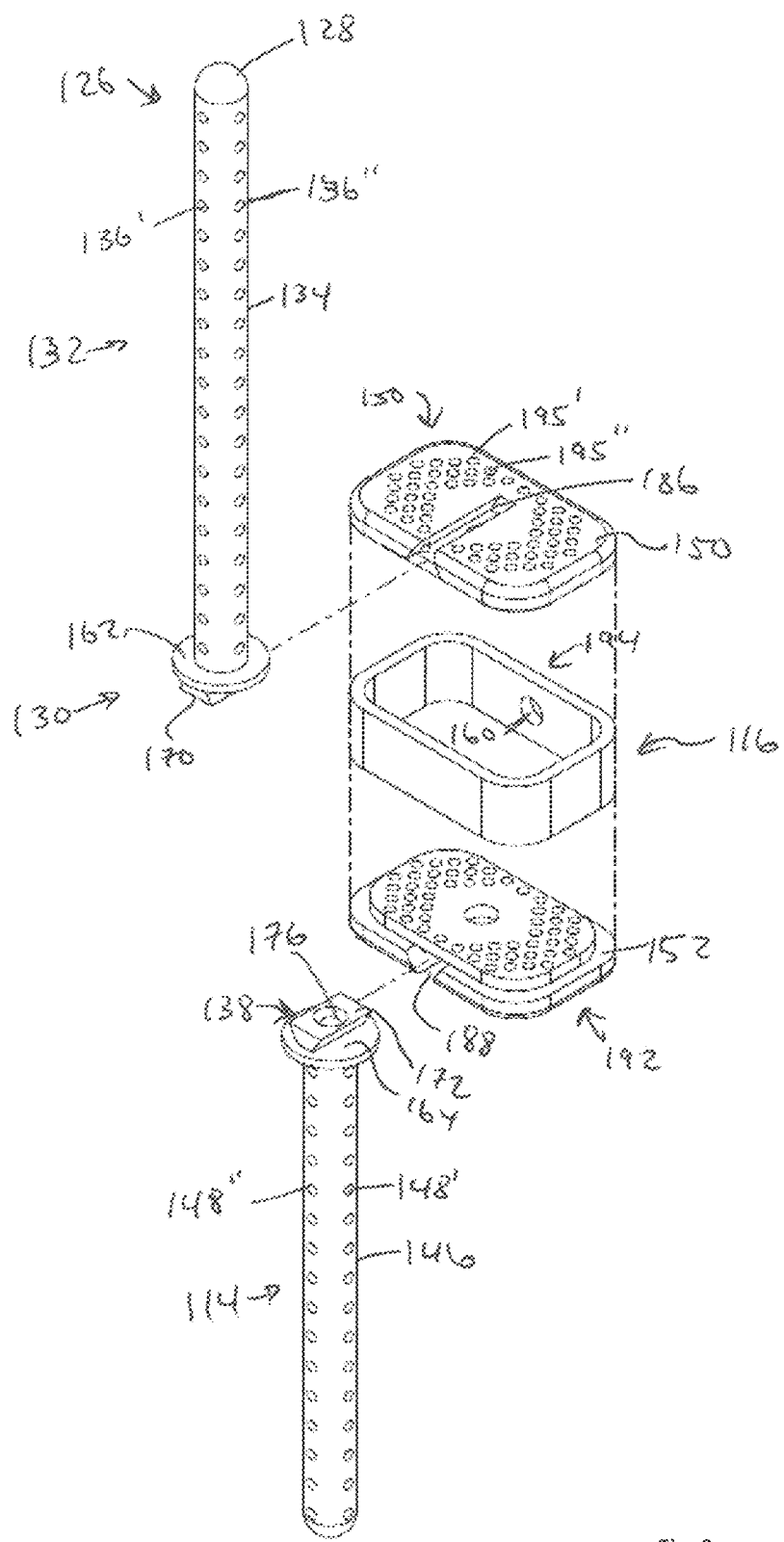
FIG. 9 is an exploded view of an embodiment of the present invention.

As with the other embodiments describes above, at least one opening 160 of coupler 116 is in fluid communication with the plurality of openings 136 and 148 of respective shafts 134 and 146 for fluid to flow through openings 136 and 148. In embodiments with fasteners 170 and 172, the at least one opening of each of the fasteners is in fluid communication with coupler opening 160 to provide a passageway for fluid to flow through openings 136 and 148 via the openings of respective fasteners 170 and 172. As depicted in FIG. 9, one face of coupler 116 comprises a fastener 186 that is complementary to fastener 170 of first rod 112 and an opposing face of coupler 116 comprises a fastener 188 that is complementary to fastener 172 of second rod 114. As such, the fasteners of the coupler mate with the fasteners of the first and second rod. The fastening mechanism between the coupler and the first and second rods may be such that the coupler is removably coupled to the rods.

The fastening connection between the coupler and the rods can be any type of fastening connection that allows the rods to be securably coupled to the rod in an operative configuration of the system. The fastening connection may be a male/female connection. For example, and as depicted in FIG. 9, fastener 170 and fastener 172 may comprise male fasteners and fasteners 186 and 188 of coupler 116 may comprise female fasteners. As depicted in FIG. 9, fastener 170 and fastener 172 may comprise a male dovetail fastener and fastener 186 and fastener 188 may comprise a female dovetail fastener. Although FIG. 9 depicts superior face 150 and inferior face 152 of coupler 116 comprising fasteners 186 and 188 respectively, any opposing faces of the coupler can comprise the fasteners that mate with the fasteners of the first and second rods, so long as fluid flow to the plurality of the rods' openings is not blocked.

With respect to any of the embodiments described above, the fenestrated coupler can have a plurality of through-holes on any face of the coupler so long as fluid is able to flow into the joint space of the patient. In the embodiments shown in FIGS. 4 and 9, through-holes 95/195 are on the superior and inferior face of the coupler but could also or instead be on other faces. Referring to FIGS. 4 and 9, in certain embodiments, the superior face of the coupler comprises a removable endplate 90/190 and the inferior face comprises a removable endplate 92/192. A spacer 94/194 is positioned between the two endplates in an operative configuration of the system. Systems of the present invention can comprise spacers of various heights, widths and other dimensions depending on the patient's joint space in which the coupler is inserted. The spacer may help maintain joint spacing to keep surrounding ligaments in tension during treatment to facilitate revision surgery following infection removal. Further, systems can comprise rods of various diameters and lengths to accommodate the particular patient's body.

With respect to any of the embodiments above, a system of the present invention also may comprise a therapeutic fluid source and a pump source. The therapeutic fluid source and pump source are shown schematically in FIGS. 10 as 196 and 198, respectively. Systems can also or instead comprise a vacuum source or an integrated pump/vacuum source, which would be used similarly to the depicted therapeutic fluid source and pump source. The pump is in fluid communication with the therapeutic fluid source and may be connected either directly or indirectly to at least one opening of the coupler to control the delivery of the therapeutic fluid to at least one opening of the coupler in an operative configuration of the system. A system can also comprise a vacuum source connected either directly or indirectly to the coupler to extract fluid from the opening of the coupler. As mentioned above, systems of the present invention can comprise an integrated pump and vacuum device that is in fluid communication with the therapeutic fluid source and with the coupler's opening. The pump controls the delivery of the therapeutic fluid to the coupler's opening and the vacuum controls the extraction of fluid from the coupler's opening. The therapeutic fluid can be any fluid that will treat the infection of the infection site, such as antibiotics and other medications.

Figure 10:
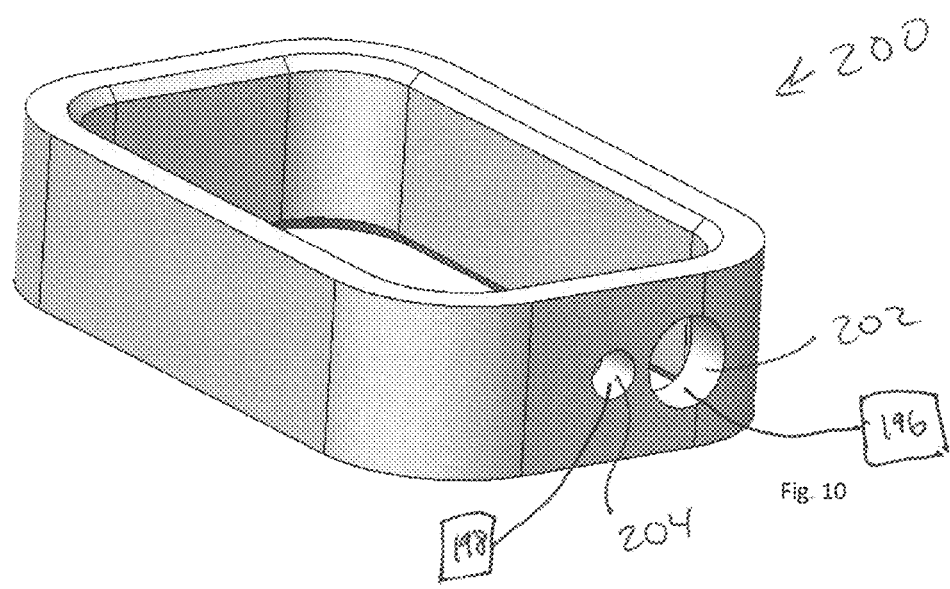
FIG. 10 is a first perspective view of a component for use with any embodiment of the present invention.
Figure 11:
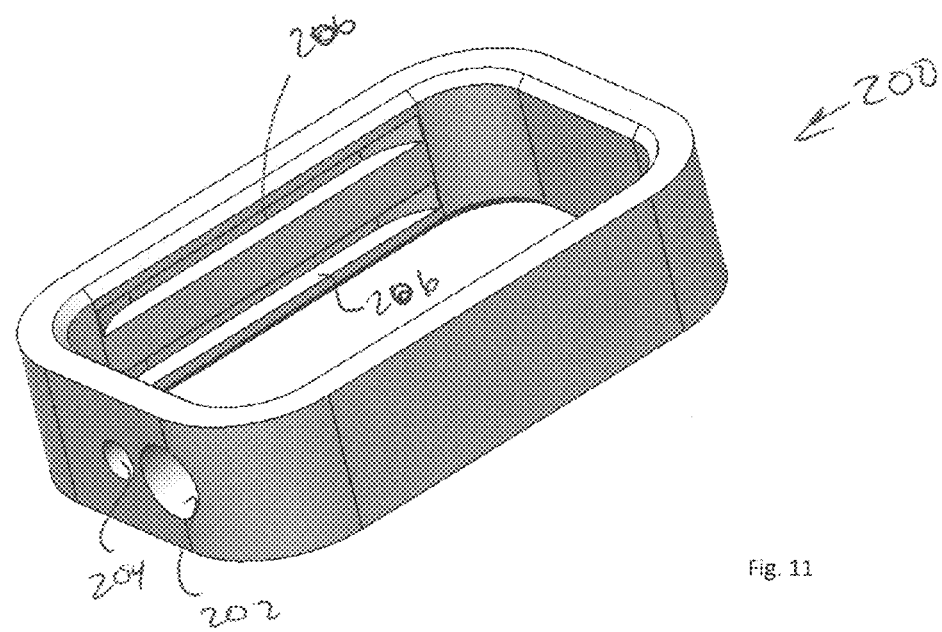
FIG. 11 is a second perspective view of the component of FIG. 10.

FIGS. 10-11 depict a component which can be used with any embodiment of the present invention. While the component of FIGS. 10-11 is shown as a spacer 200 for clarity, similar features could be provided to any type of fenestrated coupler (integral or modular) of the present invention.

In FIGS. 10-11, the spacer 200 is shown as having first and second openings 202 and 204, respectively. Any number of openings could be provided, and need not be matched in shape, size, configuration, location on the coupler face(s), or any other physical property. For example, when two openings are provided, the first opening 202 may be used to provide fluid to the system under positive pressure concurrently or sequentially with the second opening 204 removing fluid from the system under negative/vacuum pressure.

FIG. 11 also depicts a plurality of undercuts 206 on an inner surface of the spacer 200. An undercut 206 or other desired structure may be provided as a coupling securement feature. The coupling securement feature may be configured to accept a corresponding removable endplate securement feature of an endplate in an interlocking fashion. For example, endplate 208 shown in FIG. 12 includes a tab or fin 210 which "snaps" into the undercut 206 of the spacer 200. One of ordinary skill in the art can readily provide a coupling securement feature and removable endplate securement feature that cooperatively engage and thereby resist removal of that endplate 208 from the fenestrated coupler (e.g., under flexion pressure from the patient). It is contemplated, though, that for most use environments of the present invention, the user will be able to selectively disengage and engage the coupling securement feature and removable endplate securement feature, optionally without the use of tools. Optionally, at least one of the coupling securement feature and removable endplate securement feature will include a frangible and/or permanently locking structure which can be used to indicate that a system component was already used and/or prevent re-use of the system components.

Figure 12:
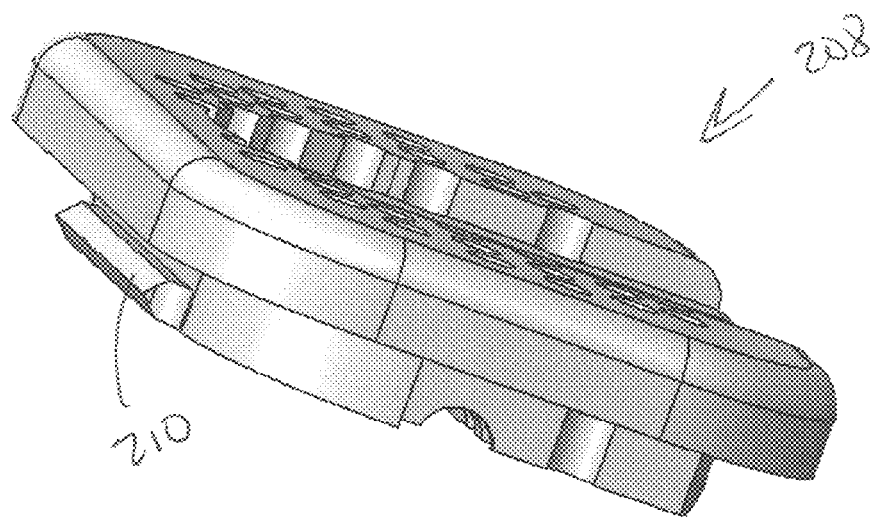
FIG. 12 is a first perspective view of a component for use with any embodiment of the present invention.
Figure 13:
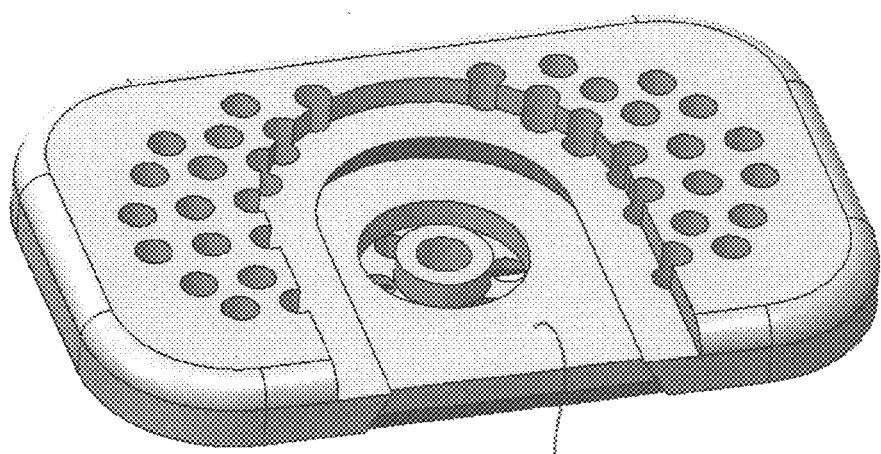
FIG. 13 is a second perspective view of the component of FIG. 12.

FIGS. 12-14 depict an endplate 208 having a fastener 212 which is of a dovetail variety, like those previously described, but accommodates a circular fastener 214, such as that shown in the partial intramedullary rod 216 view of FIG. 15. (Intramedullary rod 216 can be a first and/or second intramedullary rod and can be used, along with endplate 208, with any embodiment of the present invention.)

Because of the round or circular nature of the mating fasteners 212 and 214, it is possible for a user to dictate a rotational position of the intramedullary rod 216 with respect to the endplate 208. Thereby, the user may selectively allow or block passage of fluid communication between the openings 218 of the endplate 208 and the grooves 220 around the periphery of the shaft of the intramedullary rod 216 by simply rotating the intramedullary rod 216 until the openings 218 line up, or are misaligned, with the grooves 220 and/or any intermediate features of the intramedullary rod 216. It is contemplated that the openings 218 and grooves 220 may be selectively aligned to help control an amount of fluid flow permitted therebetween.

The central opening 222 of the endplate 208 is placed in fluid communication with the lumen 224 of the intramedullary rod 216 when the fasteners 212 and 214 are mated. Fluid communication is thus established from the central opening 222, through the lumen 224 and to the lumen openings 226 at/near the outboard end of the intramedullary rod 216, as shown in FIGS. 16-17.

Via the arrangement shown in FIGS. 14-17, then, and with the optional assistance of appropriate structure (not shown) within the coupler or elsewhere in the system, fluid can be directed from the central opening 222 of the endplate 208, through the lumen 224 and out the lumen openings 226, wherein an appropriately configured pressure gradient will urge the fluid back down the grooves 220 and into the openings 218 of the endplate 208 in a circulating matter within the intramedullary space.

FIGS. 18-21 depict components of an infection treatment system which is similar to, but simpler than, that shown in FIGS. 14-17. In FIG. 18, an endplate 228 has openings 230 but lacks a central opening like that described with reference to FIG. 14. The openings 230 of FIG. 18 can be selectively lined up or misaligned (depending upon the type and amount of fluid flow/blockage desired) with corresponding openings 232 of an intramedullary rod 234. The openings 232 are in fluid communication with the grooves 236 of that intramedullary rod 234. Therefore, supply and/or removal of fluid from the area surrounding the intramedullary rod 234 can be accomplished through the grooves 236 responsive to pressure gradients applied at/near the base, not the tip, of the intramedullary rod 234, in contrast to the "cyclical" or concurrent fluid supply/removal arrangement provided in FIGS. 14-17. The configuration of FIGS. 18-21 will likely be used for alternating or sequential fluid supply/removal through switching of pressure directions through the openings 230 and 232, but it is also contemplated that some of the openings 230 and 232 may be used for fluid supply concurrently with others of the openings 230 and 232 being used for fluid removal.

Figure 22:
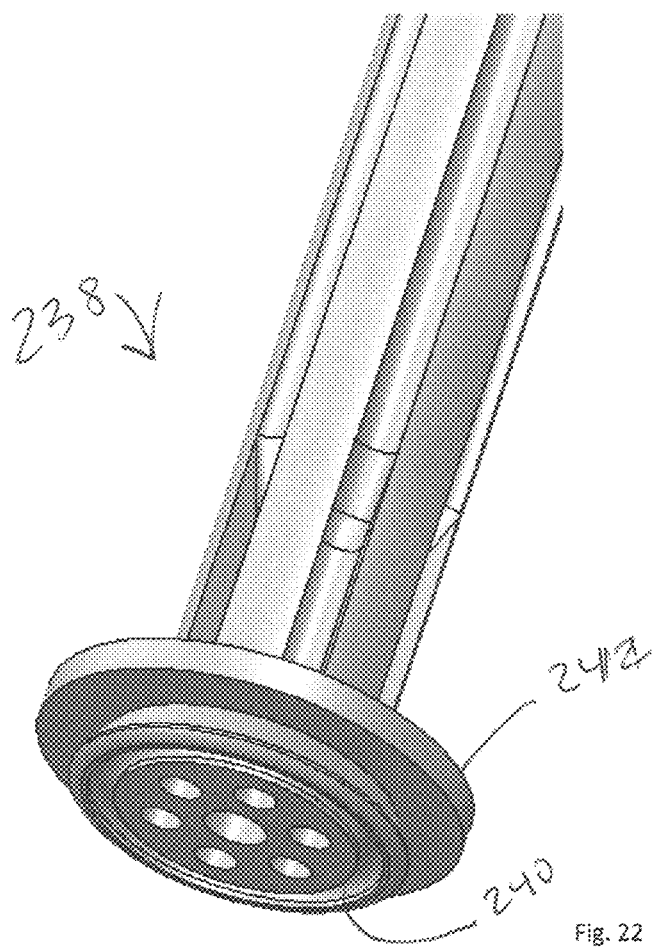
FIG. 22 is a partial perspective view of another component for use with any embodiment of the present invention.
Figure 23:
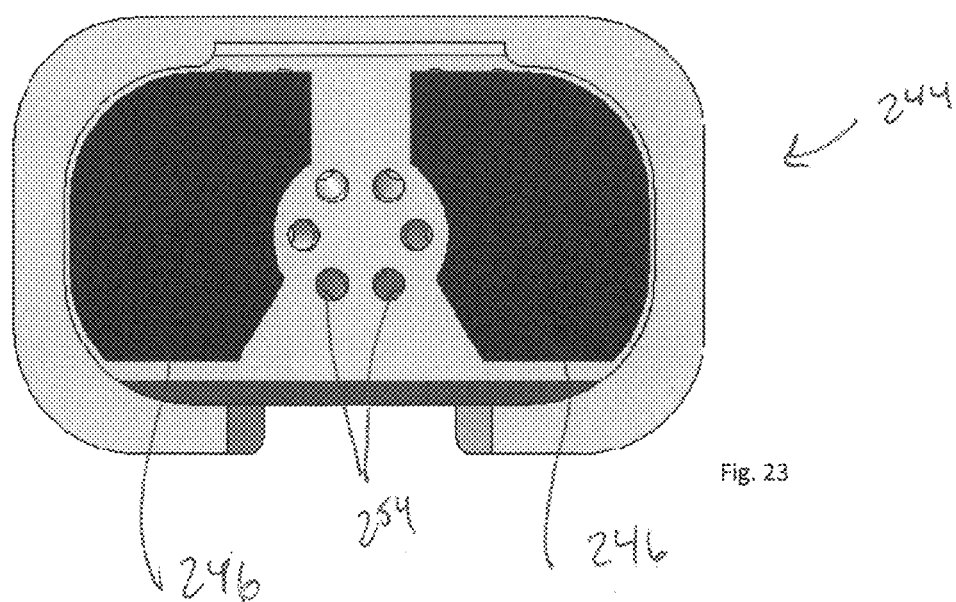
FIG. 23 is a plan view of another component for use with any embodiment of the present invention.

FIG. 22 depicts a base portion of an intramedullary rod 238 with a dovetail-type fastener 240. The fastener 240 may be round/circular in nature to facilitate rotational positioning as desired, to assist with alignment and/or engagement with a mating fastener (not shown) of an endplate (not shown), and/or for any other reason. While FIG. 22, like all Figures herein, is not necessarily shown to scale, FIG. 22 also depicts a disk 242 which has a larger diameter than any other portion of the intramedullary rod 238. One function of this "flange" type disk 242 may be to serve as a "stop" to prevent the intramedullary rod 238 from being inserted or drawn too deeply into the intramedullary space/canal of the patient's bone. Optionally, the disk 242, when present, may be longitudinally movable along the shaft of the intramedullary rod 238 to dictate a length of the intramedullary rod 238 which is permitted to enter the intramedullary space/canal.

FIGS. 23-29 depict an endplate 244 having one or more diversion members (two flaps 246 shown) which are configured to selectively block at least one opening 248 of the coupler (here, of the endplate 244) from fluid communication with at least a portion of the plurality of grooves 250 of the intramedullary rods 252 responsive to fluid pressure applied to the coupler in an operative configuration of the system. In the depicted configuration of FIGS. 23-29, the flaps 246 are flexible and are anchored adjacent to, but are not operatively connected with, a group of openings 254 which are in linear fluid communication with the grooves 250. One of ordinary skill in the art will be able to provide suitable diversion member(s) which block selected ones, or all, of the total openings 248 and 254 of an endplate 244.

Figure 24:
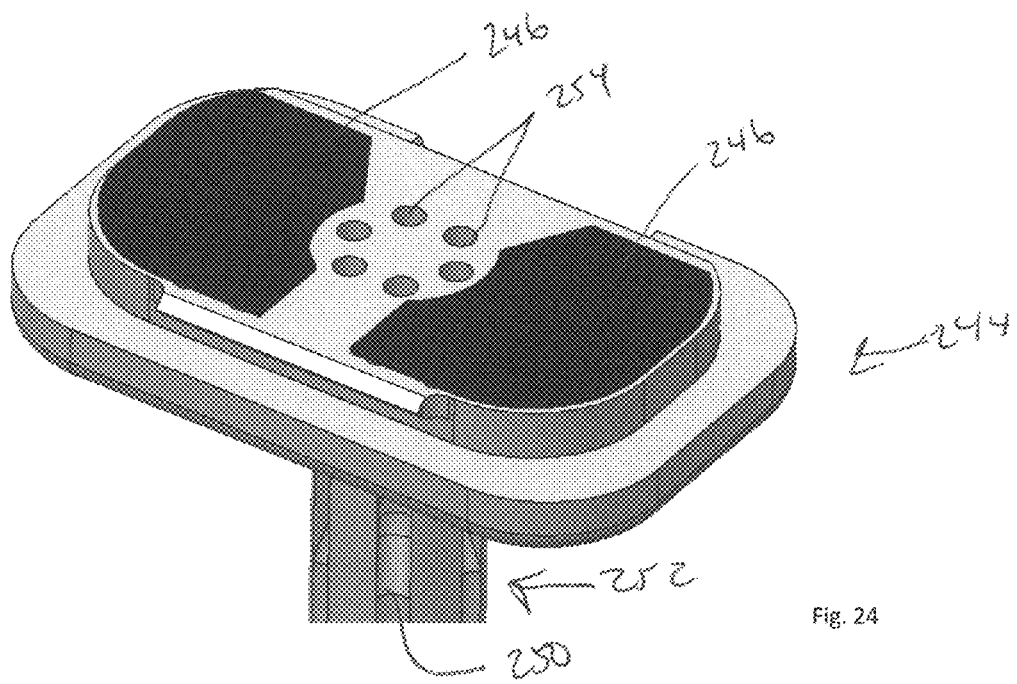
FIG. 24 is a perspective view of the component of FIG. 23.
Figure 25:
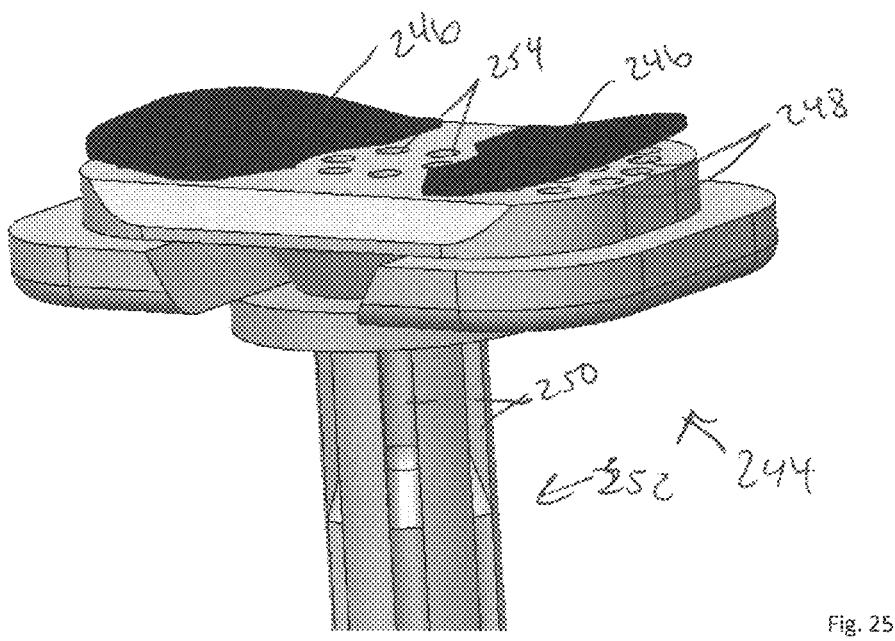
FIG. 25 is a side view of the component of FIG. 23.
Figure 27:
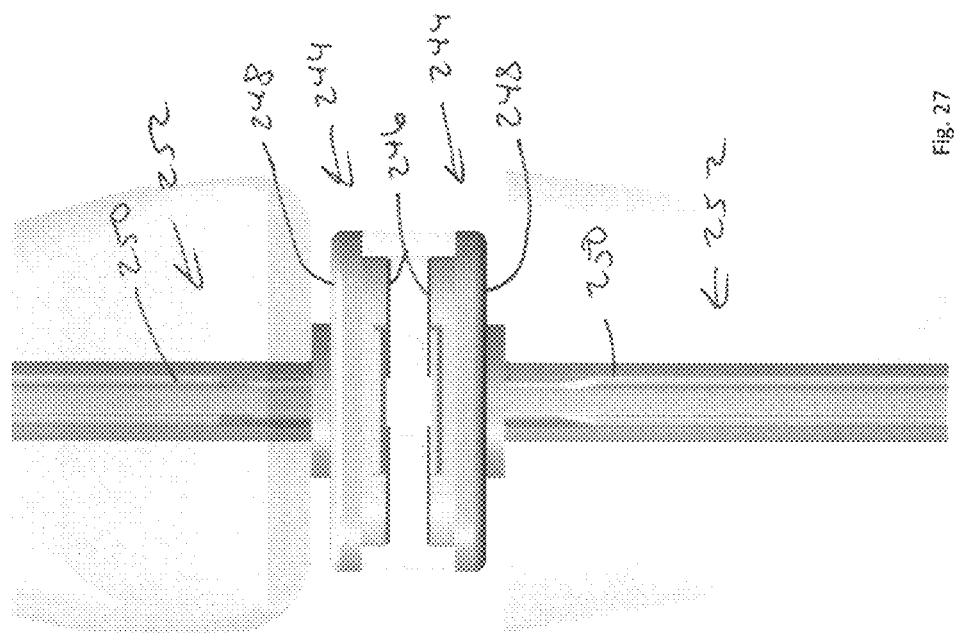
FIG. 27 is a side view of the component of FIG. 23 in the first operating mode in the example use environment.
Figure 26:
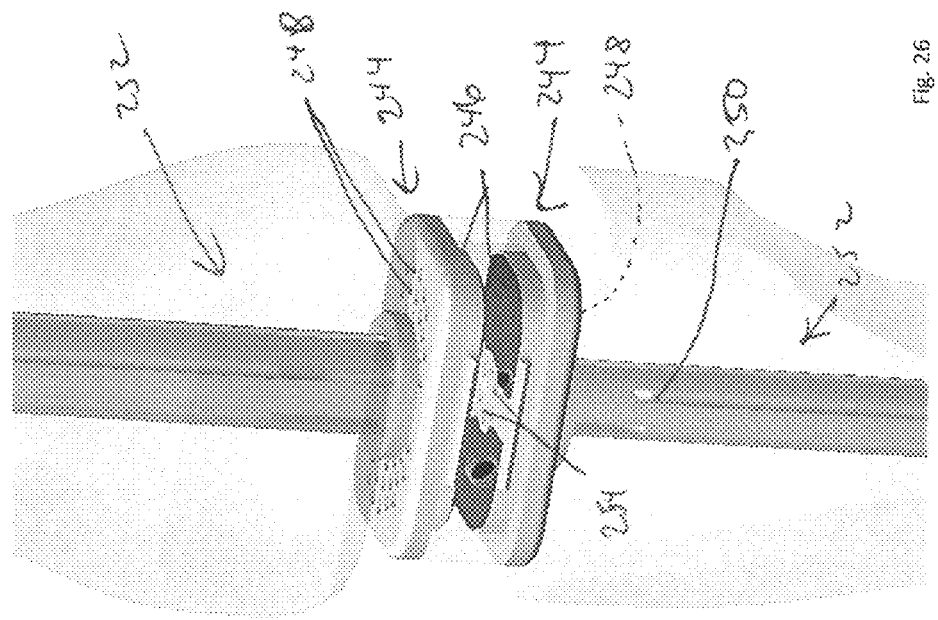
FIG. 26 is a perspective view of the component of FIG. 23 in a first operating mode in an example use environment.
Figure 29:
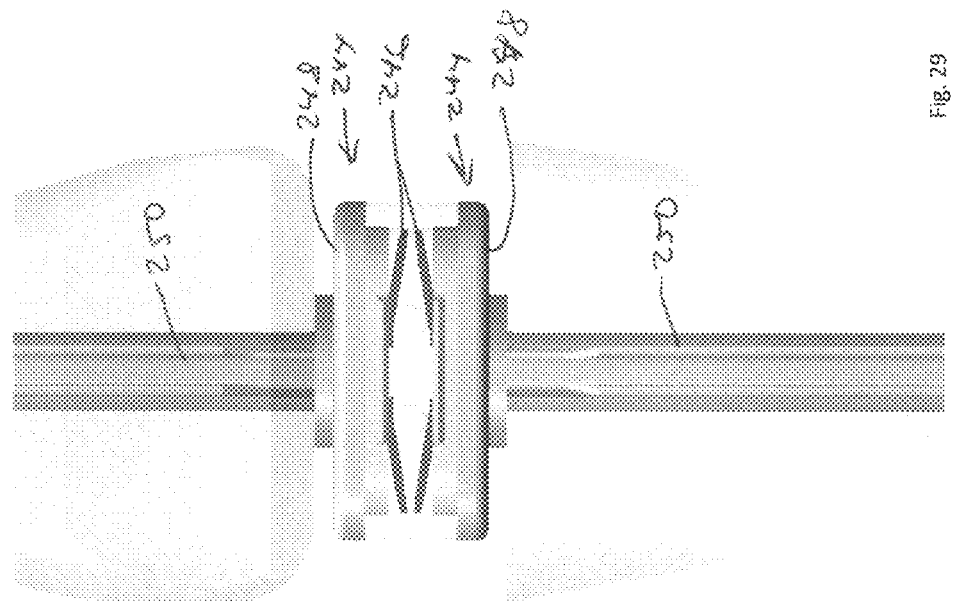
FIG. 29 is a side view of the component of FIG. 23 in the second operating mode in the example use environment.
Figure 28:
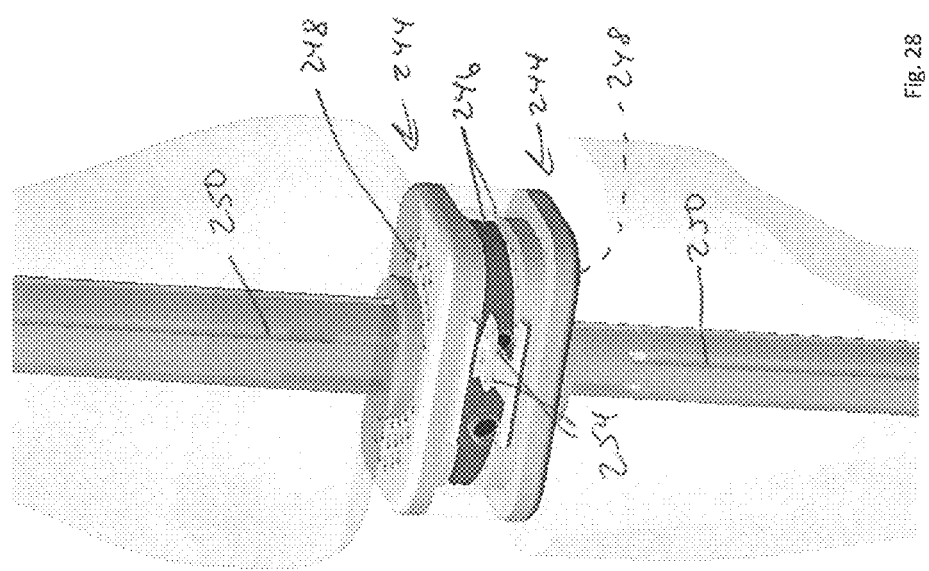
FIG. 28 is a perspective view of the component of FIG. 23 in a second operating mode in the example use environment.

As shown in FIG. 24, the flaps 246 may be "down" (i.e., covering and preventing fluid flow from within the coupler to openings 248) when there is positive pressure building/present within the body of the coupler. In this manner, fluid can be substantially diverted/directed through unblocked openings, such as those openings 254 in linear fluid communication with the grooves 250, and substantially prevented from passing through the openings 248 into the joint space adjacent to the coupler other than through the grooves 250 and corresponding openings 254. This arrangement is shown in vivo in FIGS. 26-27.

When a negative pressure is then building/present within the body of the coupler, the flaps 246 are then urged "up" and away from the openings 248 to permit fluid flow therethrough, from the joint space around the coupler into the coupler and likely out of the patient's body under the vacuum system. There may also be a fluid flow path into the coupler through the grooves 250 and communicating openings 254 concurrently with the fluid flow path through the openings 248 permitted by the "disengaged" flaps 246. This arrangement is shown in vivo in FIGS. 28-29.

One of ordinary skill in the art can readily configure one or more flaps 246 or other diversions members/mechanisms, located anywhere on the infection treatment system and operative to selectively block any number/type of openings under appropriate pressure, for a particular use environment of the present invention. For example, diversion mechanisms could be located on outer (patient-tissue-adjacent) surfaces of the coupler, in selective blocking engagement with a central opening or a rod lumen, or in any other configuration position, as desired.

One example method of employing a system of the present invention will now be described with respect to a patient who has undergone TKA and subsequently developed an infection in and/or around the implantation site. The method is described with respect to the embodiment of the invention depicted in FIG. 4 but it is understood that the method can apply to any of the above-described embodiments. Further, the order of the steps of the following method can be modified.

According to this example embodiment, the total knee prosthetic is removed from the patient and the joint space is irrigated to remove as much infection material as possible. The femoral intramedullary canal can be reamed to size and the respective femoral rod chosen by the physician, optionally from an array of femoral rods having various dimensions. Likewise, the tibal intramedullary canal can be reamed to size and the respective tibial rod chosen, optionally from an array of tibial rods having various dimensions. The femoral and tibial rods can be inserted into the respective canals and the fasteners, such as the dovetails of the rods, can be aligned to receive the coupler and then the coupler can be slid into the patient's joint space. As mentioned above, the coupler allows the physician to restore the joint space while retaining tension on the surrounding ligament structures during the infection treatment.

A therapeutic fluid, such as an antibiotic, can be delivered to the coupler, such as via an integrated pump/vacuum device that is in fluid communication with a therapeutic fluid source and in fluid communication with at least one of the coupler's openings. The fluid flows through the coupler's opening(s) and through the plurality of openings of the fastener of the first rod and the plurality of openings of the fastener of the second rod. The fluid also flows through the plurality of apertures of the base plates of the first and second rod. The fluid enters the plurality of channels of the rods' shafts to irrigate the intramedullary canals. The fluid generally can enter the joint space around the infection treatment system via the openings of the coupler and/or the rod(s). The groove and stopper of the rods in conjunction with the base plates of the rods allow the fluid to flow within and between the channels. The groove and stopper of the rods prevent fluids from flowing past the shafts essentially controlling fluid flow within and between the channels. The through-holes of the coupler allow fluid to irrigate the joint space. Thus, a system of the present invention allows for both treatment of the intramedullary canals as well as the joint space.

The fluid can bathe and/or circulate at/near the infection site until the physician decides to remove the fluid. In this method, the fluid introduced into the intramedullary canals and joint space can be removed by activating the vacuum of the integrated pump/vacuum device or otherwise applying negative pressure to extract fluid from the canals and joint space. This process of introduction and extraction of the antibiotic fluid can be concurrent, so that the antibiotic fluid is continually transferred into the infection site and extracted from the infection site, or can be done sequentially, with fluid being provided and then extracted in an alternative fashion. The intramedullary rods and coupler can remain in the patient until the infection has been treated or the physician otherwise determines that the rod and coupler should be removed. Once removed, a new total knee prosthetic can be implanted in the patient.

While aspects of the present invention have been particularly shown and described with reference to the embodiments above, it will be understood by those of ordinary skill in the art that various additional embodiments may be contemplated without departing from the spirit and scope of the present invention. For example, the specific methods described above for using the described system(s) and device(s) are merely illustrative; one of ordinary skill in the art could readily determine any number of tools, sequences of steps, or other means/options for placing the above-described apparatus, or components thereof, into positions substantially similar to those shown and described herein. Any of the described structures and components could be integrally formed as a single piece or made up of separate sub-components, with either of these formations involving any suitable stock or bespoke components and/or any suitable material or combinations of materials; however, the chosen material(s) should be biocompatible for most applications of the present invention. Though certain components described herein are shown as having specific geometric shapes, all structures of the present invention may have any suitable shapes, sizes, configurations, relative relationships, cross-sectional areas, or any other physical characteristics as desirable for a particular application of the present invention. The endplates and intramedullary rods may be configured to operate interchangeably with either a femoral or tibial side of a coupler, or may be at least partially side-specific. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. Any of the components described herein could have a surface treatment (e.g., texturization, notching, etc.), material choice, and/or other characteristic chosen to provide the component with a desired interaction property (e.g., tissue ingrowth, eluting of a therapeutic material, etc.) with the surrounding tissue. A device or method incorporating any of these features should be understood to fall under the scope of the present invention as determined based upon the claims below and any equivalents thereof. Other aspects, objects, and advantages of the present invention can be obtained from a study of the drawings, the disclosure, and the appended claims.

Having described the invention, we claim:

1. An infection treatment system comprising:
a first intramedullary rod configured for placement within an intramedullary canal, the first rod comprising a superior portion having a superior end, an inferior portion having an inferior end, and a shaft having a longitudinal axis therethrough and extending between the superior and inferior portions, the shaft comprising a plurality of elongate angularly spaced channels extending substantially parallel to the longitudinal axis of the shaft;
a second intramedullary rod configured for placement within an intramedullary canal, the second rod comprising a superior portion having a superior end, an inferior portion having an inferior end, and a shaft having a longitudinal axis therethrough extending between the superior and inferior portions, the shaft comprising a plurality of elongate angularly spaced channels extending substantially parallel to the longitudinal axis of the shaft; and
a fenestrated coupler attached to the first and second rods in an operative configuration, the fenestrated coupler having a superior face, an inferior face, an anterior face, a posterior face, a first lateral face and a second lateral face, at least one of the faces comprising at least one opening in fluid communication with at least a portion of the plurality of channels of the first and second rods, the fenestrated coupler includes at least one coupling securement feature configured to accept a corresponding removable endplate securement feature of an endplate in an interlocking fashion and thereby resist removal of that endplate from the fenestrated coupler.

2. The infection treatment system of claim 1, further comprising:
a therapeutic fluid source; and
a pump in fluid communication with the therapeutic fluid source and connected to at least one opening of the coupler to control the delivery of the therapeutic fluid to the opening of the coupler in an operative configuration of the system.

3. The infection treatment system of claim 1, further comprising a vacuum connected to at least one opening of the coupler to extract fluid from the opening of the coupler in an operative configuration of the system.

4. The infection treatment system of claim 1, further comprising:
a therapeutic fluid source; and
an integrated pump and vacuum device, wherein in an operative configuration of the system, the device is in fluid communication with the therapeutic fluid source and connected to at least one opening of the coupler, the pump controlling the delivery of the therapeutic fluid to at least one opening of the coupler, the vacuum controlling the extraction of fluid from at least one opening of the coupler.

5. The infection treatment system of claim 1, wherein the superior face comprises a removable endplate and the inferior face comprises a removable endplate, each of the endplates comprising a plurality of through-holes.

6. An infection treatment system comprising:
a first intramedullary rod configured for placement within an intramedullary canal, the first rod comprising a superior portion having a superior end, an inferior portion having an inferior end, and a shaft having a longitudinal axis therethrough and extending between the superior and inferior portions, the shaft comprising a plurality of elongate angularly spaced channels extending substantially parallel to the longitudinal axis of the shaft, the inferior portion comprising a base plate defining an array of apertures in fluid communication with the plurality of channels and comprising a fastener depending from the base plate, the fastener comprising at least one opening in fluid communication with the array of apertures, the superior portion comprising a circumferential groove and a stopper superior to the groove, the stopper having an outer diameter equal to or greater than the outer diameter of the shaft;

a second intramedullary rod configured for placement within an intramedullary canal, the second rod comprising a superior portion having a superior end, an inferior portion having an inferior end, and a shaft having a longitudinal axis therethrough and extending between the superior and inferior portions, the shaft comprising a plurality of elongate angularly spaced channels along the longitudinal axis of the shaft, the superior portion comprising a base plate defining an array of apertures in fluid communication with the plurality of channels and comprising a fastener extending from the base plate, the fastener comprising at least one opening in fluid communication with the array of apertures, the inferior portion comprising a circumferential groove and a stopper inferior to the groove, the stopper having an outer diameter equal to or greater than the outer diameter of the shaft; and a fenestrated coupler having a superior face, an inferior face, an anterior face, a posterior face, a first lateral face and a second lateral face, a first one of the faces comprising an opening in fluid communication with at least one of the arrays of apertures of the first and second rods, and a second one of the faces comprising a fastener complementary to the fastener of the first rod and an opposing third one of the faces comprising a fastener complementary to the fastener of the second rod.

7. The infection treatment system of claim 6, further comprising:
a therapeutic fluid source; and
a pump in fluid communication with the therapeutic fluid source and connected to the opening of the coupler to control the delivery of the therapeutic fluid to the opening of the coupler in an operative configuration of the system.

8. The infection treatment system of claim 6, further comprising a vacuum connected to the opening of the coupler to extract fluid from the opening of the coupler in an operative configuration of the system.

9. The infection treatment system of claim 6, further comprising:
a therapeutic fluid source; and
an integrated pump and vacuum device, wherein in an operative configuration of the system, the device is in fluid communication with the therapeutic fluid source and connected to the opening of the coupler, the pump controlling the delivery of the therapeutic fluid to the opening of the coupler, the vacuum controlling the extraction of fluid from the opening of the coupler.

10. The infection treatment system of claim 8, wherein the therapeutic fluid is an antibiotic.

11. The infection treatment system of claim 7, wherein the opening of the coupler is located on the anterior face of the coupler.

12. The infection treatment system of claim 7, wherein the superior face of the coupler comprises a removable superior endplate and the inferior face comprises a removable inferior endplate, each of the endplates comprising a plurality of through-holes.

13. The infection treatment system of claim 12, further comprising a spacer positioned between the superior endplate and the inferior endplate and removably mated thereto.

14. The infection treatment system of claim 6, wherein the array of apertures of the first rod's base plate and the array of apertures of the second rod's base plate are in registration with the shaft's plurality of channels.

15. The infection treatment system of claim 6, wherein the at least one opening of the first rod's fastener is a plurality of openings and the at least one opening of the second rod's fastener is a plurality of openings.

16. The infection treatment system of claim 6, wherein the first and second rod's fasteners are male dovetail fasteners and the fastener of the one of the faces and the opposing one of the faces of the coupler are female dovetail fasteners.

17. The infection treatment system of claim 6, wherein the first and second rod's fasteners are male dovetail fasteners and the fastener of the second one of the faces and the opposing third one of the faces of the coupler are female dovetail fasteners.

18. The infection treatment system of claim 17, wherein the second one of the faces is the superior face of the coupler and the opposing third one of the faces is the inferior face of the coupler.

19. The infection treatment system of claim 6, wherein the superior face of the coupler comprises a removable superior endplate and the inferior face comprises a removable inferior endplate, each of the endplates comprising a plurality of through-holes.

20. The infection treatment system of claim 19, further comprising a spacer positioned between the superior endplate and the inferior endplate and removably mated thereto.

21. The infection treatment system of claim 19, wherein the fenestrated coupler includes at least one coupling securement feature configured to accept a corresponding removable endplate securement feature of an endplate in an interlocking fashion and thereby resist removal of that endplate from the fenestrated coupler.

* * * * *